United States Patent
Meftah et al.

(10) Patent No.: US 10,219,747 B2
(45) Date of Patent: Mar. 5, 2019

(54) APPARATUS AND METHOD TO SUPPRESS OR PREVENT FALSE ALARMS IN AN ESOPHAGEAL TEMPERATURE PROBE AND FEEDING TUBE

(71) Applicant: KONINKLIJKE PHILIPS N.V., Eindhoven (NL)

(72) Inventors: Mohammed Meftah, Tilburg (NL); Edwin Gerardus Johannus Maria Bongers, Thorn (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 159 days.

(21) Appl. No.: 15/104,784

(22) PCT Filed: Dec. 18, 2014

(86) PCT No.: PCT/IB2014/067070
§ 371 (c)(1),
(2) Date: Jun. 15, 2016

(87) PCT Pub. No.: WO2015/092733
PCT Pub. Date: Jun. 25, 2015

(65) Prior Publication Data
US 2017/0000420 A1    Jan. 5, 2017

Related U.S. Application Data

(60) Provisional application No. 61/917,670, filed on Dec. 18, 2013.

(51) Int. Cl.
*A61B 5/05*    (2006.01)
*A61B 5/00*    (2006.01)
(Continued)

(52) U.S. Cl.
CPC ........... *A61B 5/6852* (2013.01); *A61B 5/01* (2013.01); *A61B 5/02055* (2013.01);
(Continued)

(58) Field of Classification Search
CPC ........ A61M 5/168; A61M 5/142; A61B 5/05; A61B 5/00; A61B 5/0205; A61B 5/03; A61B 5/042; A61J 15/00
(Continued)

(56) References Cited

U.S. PATENT DOCUMENTS

2010/0036229 A1    2/2010  Weekamp
2010/0082011 A1    4/2010  Lewis
(Continued)

FOREIGN PATENT DOCUMENTS

WO    2006/015230    2/2006

*Primary Examiner* — Carl H Layno
*Assistant Examiner* — Jon Eric C Morales (57) ABSTRACT

A method of preventing or suppressing a false alarm during administration of food or medicine to a human or animal through a feeding tube having one or more sensors that generate a signal, comprises analyzing the signals to determine whether food or medicine is being administered and, if it is determined that food or medicine is present, preventing or suppressing an alarm. In a further step, the time and length of administration of food or medicine is recorded. When the feeding tube has at least two temperature sensors, differences in the temperatures recorded for the different temperature sensors indicate that food or medicine was administered. In a case where there is only one temperature sensor, the rate and extent of any temperature change of temperatures recorded from that temperature sensor are compared to an algorithm to determine whether feeding occurred. If the feeding tube has two or more electrodes that sense a change in impedance (galvanic or non-galvanic), that change indicates whether food or medicine is being admin- (Continued)

istered. The signals are analyzed by a processor, monitor, or controller that generates an alarm signal.

12 Claims, 4 Drawing Sheets

(51) Int. Cl.

| | |
|---|---|
| *A61B 5/01* | (2006.01) |
| *A61B 5/0205* | (2006.01) |
| *A61B 5/03* | (2006.01) |
| *A61B 5/042* | (2006.01) |
| *A61B 5/053* | (2006.01) |
| *A61B 5/1459* | (2006.01) |
| *A61J 15/00* | (2006.01) |
| *A61B 5/087* | (2006.01) |

(52) U.S. Cl.
CPC ............ *A61B 5/037* (2013.01); *A61B 5/0421* (2013.01); *A61B 5/0538* (2013.01); *A61B 5/1459* (2013.01); *A61B 5/4839* (2013.01); *A61B 5/7203* (2013.01); *A61B 5/746* (2013.01); *A61J 15/0003* (2013.01); *A61J 15/0084* (2015.05); *A61B 5/087* (2013.01); *A61B 2503/045* (2013.01); *A61B 2505/03* (2013.01)

(58) Field of Classification Search
USPC ........................................................ 600/424
See application file for complete search history.

(56) References Cited

U.S. PATENT DOCUMENTS

| | | |
|---|---|---|
| 2010/0087715 A1 | 4/2010 | Van Bommel |
| 2011/0144481 A1 | 6/2011 | Feer |

APPARATUS AND METHOD TO SUPPRESS OR PREVENT FALSE ALARMS IN AN ESOPHAGEAL TEMPERATURE PROBE AND FEEDING TUBE

CROSS REFERENCE TO RELATED APPLICATIONS

This application is the U.S. National Phase application under 35 U.S.C. § 371 of International Application No. PCT/IB2014/067070, filed Dec. 18, 2014, published as WO 2015/092733 on Jun. 25, 2015, which claims the benefit of U.S. Provisional Patent Application No. 61/917,670 filed Dec. 18, 2013. These applications are hereby incorporated by reference herein.

FIELD OF THE INVENTION

The present application relates to an esophageal feeding tube useful in patient care and, more particularly, to an apparatus and method to suppress and/or prevent false alarms in an esophageal temperature probe and feeding tube.

BACKGROUND OF THE INVENTION

When newborn babies are cared for, the size of the patient is an obvious difference when compared to the care of adult patients or other pediatric patients. Because the patient is so much smaller, instruments, sensors, and the like have to be redesigned to be used with newborn patients.

Neonates that need tube feedings typically are monitored electronically by a physiologic monitor. Such monitors use multiple electrodes and sensors adhered to the patient's chest and abdomen to capture ECG signals for calculating heart rate and for obtaining a respiration-impedance waveform for calculating respiration rate. Adhesion of skin electrodes is a problem for neonates. Not only must the adhesive have the proper electrical characteristics to transmit electrical signals, it also must adhere well enough to maintain adequate signal integrity despite motion artifacts. In addition, due to poor skin development and the criticality for fluid balance in the presence of insensible water loss (evaporation), neonates are frequently maintained in humidity and temperature controlled incubators. This not only compounds the problem of electrode adhesion but creates a need to obtain a feedback signal for the thermoregulation apparatus typically found in the incubator. Each time an electrode or sensor falls off, a caregiver must intervene immediately, which increases the workload of the care giving staff and is disruptive to the important sleep cycle of the neonate.

Further, a preterm neonate typically lacks skin integrity, and the frail skin is subject to irritation and laceration as a result of adhesives or sensors that are applied. Removal of electrodes or sensors for routine skin integrity checks and cleaning can further irritate the delicate skin of the neonate during removal. In practice, there is no perfect adhesive for a neonatal skin electrode. External electrodes and their cables also complicate routine care of the neonate (e.g., washing) and may be disturbing to parents trying to bond with the infant (a technique known as Kangaroo Care).

As with all intensive care patients, temperature changes in a neonate can indicate fever or another medical situation requiring attention. In the case of premature neonates, however, the thermoregulatory system is not yet fully developed. Therefore, unlike the temperature of an adult patient, a neonate's temperature can go into crisis within minutes (as opposed to hours for an adult) and thus must be monitored closely. Consequently, routine and continuous temperature monitoring of a neonate is conducted in the neonatal intensive care unit (NICU). Such monitoring is typically done with a thermistor probe temporarily placed in the armpit, groin, or skin. These temperature sensors entail excessive stimulation for the neonate, a factor which is believed to negatively impact development. Often, NICU patients are kept in incubators. Opening and closing the incubator to maintain temperature signals makes it difficult to maintain desired air temperature control inside an incubator.

Size can vary greatly from infant to infant. Viable premature babies are much smaller than their full term counterparts, in both weight and length. In the case of a neonatal feeding tube, the size of the tube is tailored to the size of the infant. To accommodate a range of sizes of infants, different sizes of tubes are typically required so the tip of the feeding tube rests in the stomach. Moreover, since newborn babies grow rapidly, an infant's feeding tube may need to be changed and or repositioned during the infant's stay in the NICU.

During insertion of a new feeding tube, care must be taken and verification checks made to assure that the tube has followed the esophageal path to the stomach and not the bronchial path into the lungs. Further, the opening(s) in the tube must be properly positioned in the stomach, not the esophagus, and the end of the tube must terminate before reaching the bottom of the stomach. Incorrect positioning of the feeding tube can result in aspiration of stomach contents and feeding material into the lungs, which can lead to a life-threatening lung infection or injury.

Almost all neonates staying in the NICU are fed by feeding tubes. Therefore, integration of vital signs sensors into a feeding tube can be very beneficial. For example, it eliminates the need for the standard adhesive electrodes, performs temperature spot checks, and the like. This improves the development and recovery of ill neonates, reduces the workload of caregivers, and fosters bonding between neonate and parents.

A neonatal esophageal temperature probe and feeding tube is described in U.S. Published Patent Application No. 2011/0084881, incorporated herein by reference. The feeding tube described, an embodiment of which is available as the INNERSENSE® esophageal temperature and feeding tube from Koninklijke Philips N.V., combines a neonatal feeding tube with a temperature sensor. Other vital signs sensors can optionally be integrated as well.

Figure 1:
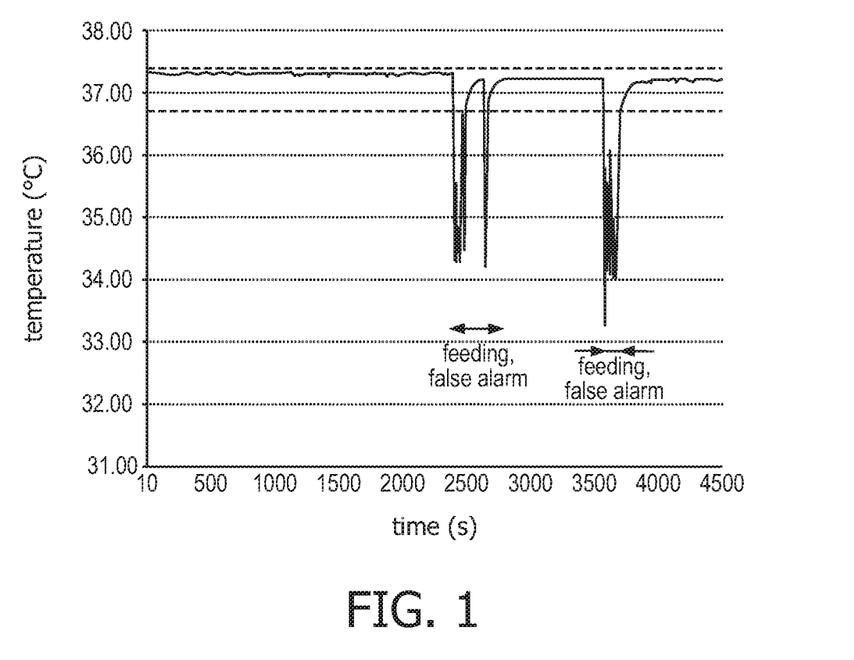
FIG. 1 represents a graph of the measured temperature of a neonate versus time.

As described above, maintaining the temperature of a neonatal is critical, and temperature sensing systems useful in the NICU are designed to generate an alarm in a neonatal's temperature suddenly increases or decreases significantly. One characteristic of current neonatal feeding tubes is that feeding itself may trigger false alarms. A clinical study was executed where an INNERSENSE feeding tube with an integrated temperature probe was used for feeding. The results of the study are set forth in FIG. 1, where it can be seen that the indicated temperature recordings were disturbed dramatically during feeding periods, when the recorded temperatures dropped below a pre-set lower temperature limit of 36.7° C. (NICU limits: 36.7-37.4° C.). However, these anomalies reflected false alarms, which counterproductively disturb and stress a neonate and worsen a caregiver's workload.

SUMMARY OF THE INVENTION

Accordingly, it is an object to overcome the deleterious effects of false alarms that may occur in the feeding and care of humans or animals.

In accordance with one aspect, temperature or other sensors in a neonatal temperature probe and feeding tube provide signals that are compared to determine whether feeding is occurring. Sensors in a feeding tube may sense a change in a parameter such as temperature, pressure, capacitance, or the like, where such change is capable of indicating whether feeding occurred. If it is determined that feeding is occurring, a change in an indicated parameter such as temperature of the neonate does not trigger an alarm.

In accordance with another aspect, a temperature or other sensor in a neonatal temperature probe and feeding tube provides a signal that is compared to an algorithm. If the signal reflects a change in the temperature of the neonate, the rate and extent of the temperature change are analyzed by an algorithm to determine whether feeding is occurring. If it is determined that feeding is occurring, a change in indicated temperature of the neonate does not trigger an alarm.

In accordance with another aspect, one or more sensors in or in a neonatal temperature probe and feeding tube provide a signal that indicates the presence of food or a liquid in a lumen of the feeding tube. If it is determined that feeding is occurring, a change in indicated temperature of the neonate does not trigger an alarm.

In accordance with another aspect, a method of preventing or suppressing false alarms in the care of a neonate comprises:
  analyzing signals from one or more sensors in a temperature probe and feeding tube to determine the presence of food or a liquid; and
  preventing or suppressing the generation of a low or high temperature alarm.

In accordance with one aspect, an esophageal temperature probe and feeding tube incorporates at least one lumen for feeding and provides a pathway for nourishment, for example, soft food or a liquid, or medicine from the outside of a subject into the stomach of the subject. At least one, but optimally two or more uniformly or non-uniformly spaced sensors are on an exterior surface of the feeding tube, within a wall of the feeding tube, or within the feeding tube for measuring temperature.

An advantage is that the neonate does not need to be disturbed unnecessarily to be treated for an apparent low or high temperature emergency.

Another advantage is that the caregiver does not need to address a perceived emergency that is not really an emergency.

Another advantage is that a caregiver's workload will not be unnecessarily increased or disturbed.

Another advantage is that the apparatus and system described herein are compatible with existing patient monitors.

Consistent with the disclosure herein, it should be appreciated that the terminology "feeding tube" comprises an orogastric or nasogastric feeding tube particularly useful in the care of a neonate for insertion through and/or into the neonate's esophagus. The feeding tube will sometimes be referred to as an esophageal feeding tube or an esophageal temperature probe and feeding tube. Also, the term "food" as used herein encompasses soft, semi-liquid, or liquid nutritional substances, including, but not limited to, formula or breast milk, given or administered to a neonate through a feeding tube. The term "food" also includes any medicine or other soft, semi-liquid, or liquid material that might be given or administered to the neonate through a feeding tube.

Still further advantages of the present invention will be appreciated to those of ordinary skill in the art upon reading and understanding the following detailed description. Therefore, it should now be apparent that the invention substantially achieves all the above aspects and advantages. Additional aspects and advantages of the invention will be set forth in the description that follows, and in part will be inherent from the description, or may be appreciated by practice of the invention. Moreover, the aspects and advantages of the invention may be realized and obtained by means of the instrumentalities and combinations particularly pointed out in the appended claims.

BRIEF DESCRIPTION OF THE DRAWINGS

The accompanying drawings illustrate presently preferred embodiments of the invention, and together with the general description given above and the detailed description given below, serve to explain the principles of the invention. As shown throughout the drawings, like reference numerals designate like or corresponding parts.

The invention may take form in various components and arrangements of components, and in various steps and arrangements of steps. The drawings are only for purposes of illustrating the preferred embodiments and are not to be construed as limiting the invention.

DETAILED DESCRIPTION OF THE INVENTION

Figure 2:
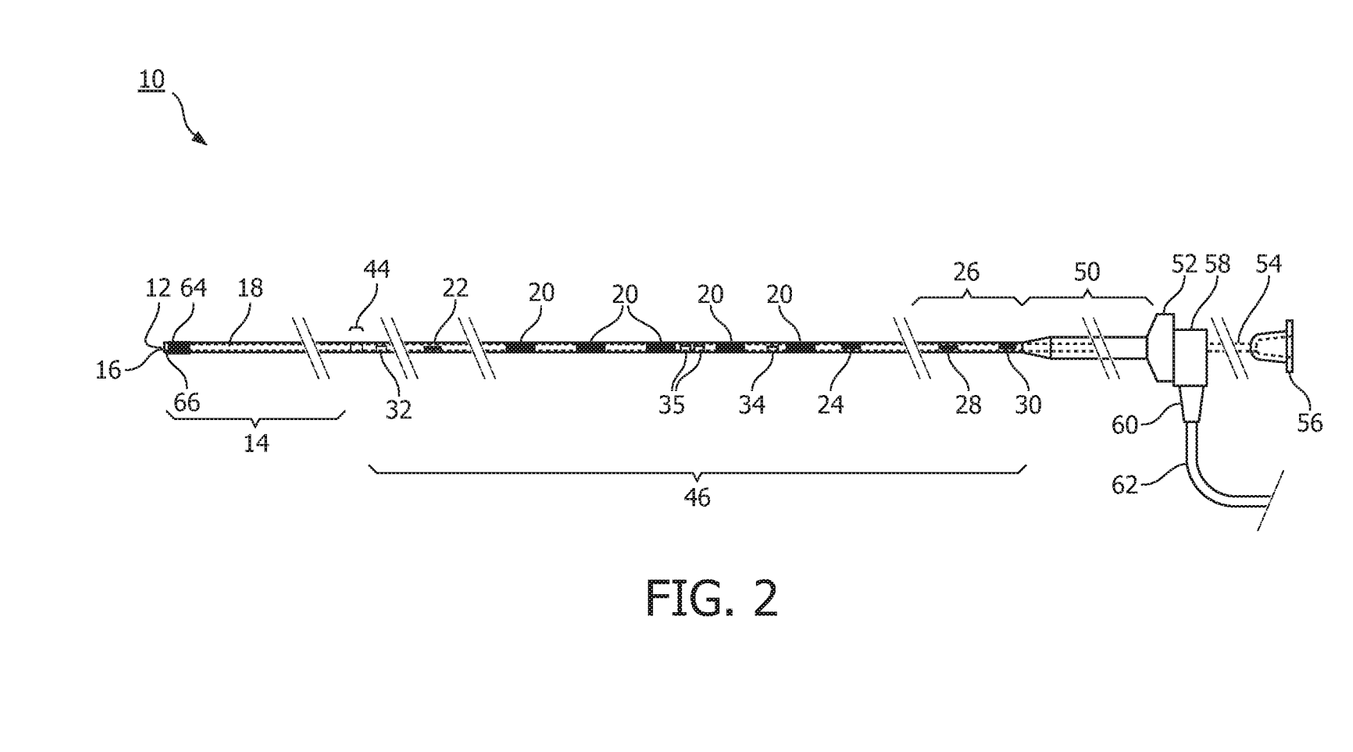
FIG. 2 represents a neonatal feeding tube with sensors and instrumentation.

The present invention, in the various embodiments described herein, relates to an apparatus, system, and method to suppress or prevent false alarms during feeding of a neonate with an esophageal temperature probe and feeding tube. The invention can perhaps be better understood from the drawings. In FIG. 2, a neonatal feeding tube 10 is depicted. In one embodiment, tube 10 is an instrumented disposable feeding tube for newborn infants (neonates) who have not yet developed their sucking capabilities, or who are unable to feed normally for some other reason. Tube 10 is a 5 French tube, or 1.67 mm in diameter, in one embodiment. Appropriate scaling can be performed for larger or smaller tubes. For convenience, tube 10 is shown segmented, though its actual length may be, for example, approximately 300 mm.

Neonates are fed formula, breast milk, or other nutritional soft, semi-liquid or liquid substances or medicines through tube 10. Tube 10 is typically inserted into the neonate's nose or mouth and advanced into the esophagus, and into the stomach. Similar to a standard feeding tube, there is a tip 12 at the distal portion 14 of tube 10. An end hole 16 in tip 12 permits soft, liquid, or semi-liquid food, such as infant formula or breast milk, or medicine to exit tube 10. One or more additional holes 18, offset from tip 12, allow food to exit should end hole 16 become clogged or otherwise blocked. Tip 12 and cross holes 18 are preferably positioned in the neonate's stomach in one embodiment. Distal portion 14 is molded of a soft, biocompatible material, such as, in one embodiment, silicone rubber.

Feeding tube 10 also includes electrodes 20. Electrodes 20 are on or within an exterior surface of feeding tube 10 and, when inserted, make contact with the patient's esophagus (not shown). Insulated leads (not shown) extend proximally from each electrode, either inside feeding tube 10 or inside the outer wall of feeding tube 10. At least one thermal sensor or thermistor 22 is inside feeding tube 10 for taking temperature measurements. In one embodiment, at least one thermistor 22 is distal to electrodes 20.

Thermistor 22 is assembled to a pair of wires, at least one of which is insulated. Preferably all wires that carry signals are insulated and located on an inner wall or the outer surface of feeding tube 10. In one embodiment, thermistor 22 is calibrated to meet the requirements of a specific patient monitor or series of monitors. Calibration is checked. Resistance is measured and compared to the specification. Resistance is then increased if necessary until the thermistor resistance meets specification. This process brings the thermistor in compliance with appropriate standards for accuracy. Thermistor 22 may be one piece of semiconductor material or it may be two or more segments connected in parallel, with a small gap between each segment. This allows the assembly to flex in two directions and to twist, even if the length is several multiples of the tube diameter. This is important, because the overall resistance of the thermistor is proportional to its thickness and inversely proportional to the area. Because the width of the thermistor and the thickness of the thermistor are constrained by the size of tube 10, the effective length of the thermistor assembly needs to be selected based on the electrical requirements of the monitoring system, without further constraint. This method of construction also minimizes difficulty and discomfort during insertion, removal, and use. It is also more flexible and more resistant to breakage during manufacture, insertion, and use. In one embodiment, thermistor 22 has a resistance of approximately $2250\Omega$ at 25° C. and approximately $1360\Omega$ at 37° C.

In a single-thermistor embodiment, thermistor 22 is preferably located in the esophagus to accurately measure core temperature, rather than the stomach or pharynx, where readings would be less accurate. Placement in the stomach is undesirable due to the corrosive effects of gastric fluids and the inaccuracy that might be caused by air or food in the stomach. Whether thermistor 22 is located distal to the electrodes, proximal to them, or among them is determined by practical design issues and patient size. However, a dual lumen with at least one thermistor in the hypopharynx can provide respiration measurement.

Proximal to electrodes 20 is a nasopharyngeal section 26 of feeding tube 10. Nasopharyngeal section 26, as the name indicates, lies inside the pharynx and nose when inserted. This section is smooth and small in diameter to avoid irritating the patient or interfering with air flow during breathing. In an alternate embodiment, however, feeding tube 10 has a non-circular shape and/or concave flutes to reduce the possibility of complete blockage of a nare. In yet another embodiment, a hypopharynx thermistor 28 and an oropharynx thermistor 30 are included in the nasopharyngeal section 26. Thermistors 28, 30 are used to measure respiration flow, in addition to the distal or caudal thermistor 22 provides a core temperature measurement. The respiration flow is measured as a relative temperature change between oropharynx thermistor 30 and hypopharynx thermistor 28. An array of these thermistor pairs may accommodate variations of patient sizes.

A pressure differential $\Delta P$ is measured by a pressure gradient between a sub-diaphragmatic (or caudal) port 32 and a supra-diaphragmatic (or cephalic) port 34. $\Delta P$ represents the respiration effort of the patient. Flow can be measured separately (with thermistors 28 and 30), as an airway obstruction may produce increased effort but no $\Delta P$. Respiration flow and respiration effort are measured separately and can differ. For example, in the case of an airway obstruction, effort will increase but flow will decrease. The measured flow can be cross-checked against $\Delta P$ for accuracy, and can signal an alarm if the two do not coincide.

Proximal to the supra-diaphragmatic pressure port 34 are two fiber optic windows 35. Fiber optic windows 35 are polished ends of many fiber optic strands. At the proximal end of feeding tube 10 fiber optic strands separate into a source fiber (run from a light source, not shown) and a return fiber. Both fiber bundles run down the interior of feeding tube 10 to fiber optic windows 35. One fiber optic bundle is in the esophagus, and another is at the distal tip of the feeding tube. The distal fiber bundle does not need to be separated into a sending and receiving bundle as it is used only to send light down which would emanate from the small patient due to the thin membranes and relatively translucent nature of the skin. This tip light is used for placement verification by energizing the fibers from an external light source and in a darkened room and visualizing the location of the light emanating from the patient's abdomen (if properly placed) or thorax (if not properly placed). The pulse of the subject is measured by reflectance photoplethysmogram through the fiber optic window using traditional reflectance pulse oximetry techniques. Core $SpO_2$ is also measured at fiber optic windows 35. Supra-diaphragmatic port 34 serves as a flush location to clean fiber optic windows 35 as needed.

The manufacture and structure of a temperature probe and feeding tube according to the invention is consistent with the manufacture and structure of the esophageal feeding tube described in U.S. Published Patent Application No. 2011/0084881, incorporated herein by reference in its entirety.

A feeding lumen extension 54 may pass through the approximate center of a tube-side connector 52 and terminates in an oral style fitting 56 that permits food such as baby formula or breast milk or medicine to be injected by syringe, drip, pump, or other means. In one embodiment, fitting 56 is marked or physically differentiated to distinguish it from ports meant for vascular injection.

Typically, only three electrodes are required for ECG readings. For small neonates, the distal three electrodes 20 are used. For medium neonates, the middle three electrodes 20 are used. For larger neonates, the proximal three electrodes 20 are used. In one embodiment, the electrodes are selected manually based on the size of the neonate, and the judgment of the caregiver. The setting can be selected by the caregiver by temporarily disconnecting the connector, rotating a cable-side part 58 relative to connector 52, and then re-connecting, thereby changing which internal contacts are used. In another embodiment, the electrodes are selected by the monitor. Once the feeding tube is inserted, all electrodes 20 send signals to a monitor (not shown). The monitor displays multiple wave-forms, and the operator selects the clearest display. In other embodiments, all signals are recorded or the monitor automatically chooses the best electrodes.

It should be noted here that respiration rate can be determined by injecting a low-voltage electrical signal into the patient via a pair of spaced ECG electrodes. The electrical impedance of the connection varies during the act of respiration, so the rate and depth of respiration can be deduced. In some embodiments of this invention, the respiration rate is derived from a choice of electrodes selected from the array of available electrodes.

In an alternate embodiment a U-shaped connector on the monitor side is used so that feeding tube 10 can be in the center, with mating in the axial direction. The U-shape allows the electrical connection and the feeding connection to be made or disconnected in any sequence, without mutual interference.

In another alternate embodiment, a connector is on the side of the feeding tube, with mating in the radial or oblique direction.

In another alternate embodiment, feeding tube 10 has a rectangular (linear) connector rather than a circular or U-shaped connector. In this embodiment, the feeding tube side would have a number of sockets (pins) equal to the number of electrodes, while the cable side would have a number of pins equal to the number of electrodes used by the monitor. The cable could then be plugged into feeding tube 10 in a number of locations, thereby selecting which electrodes are operative.

In another alternate embodiment, feeding tube 10 has a connector where the selection of the electrodes is performed by a switching device inside cable-side connector 58, or cable 62 itself.

In another alternate embodiment, feeding tube 10 has a connector with a rotating collar or other device which could be locked into place to assure that the connector, after disconnection, can only be re-connected in the selected position.

In another alternate embodiment, feeding tube 10 has a slide or rotary switch on the connector to allow the caregiver to manually select the electrodes with the strongest signal as shown on a monitor display.

Placing the tube properly can be problematic in some instances. Feeding tube 10 is to be inserted to a depth that places tip 12 of feeding tube 10 in the stomach of a neonate. It is undesirable to insert feeding tube 10 too far, into the duodenum, and it is also undesirable to leave it short, such that openings 16 and 18 are in the esophagus. A distal electrode 64 on tip 12 of feeding tube 10 is included to facilitate placement confirmation. While distal electrode 64 remains in the esophagus, contact with the wall of the esophagus produces electrical continuity. However, when this electrode passes through the esophageal sphincter into the larger opening of the stomach, conductivity disappears. Because the relative location of electrode 64 and openings 18 is established by the detailed design of the device, the location of openings 18 is now known to the clinician relative to the beginning of the patient's stomach.

In conjunction with electrode 64, a light source 66 can be used to judge the position of tip 12 as it is passed down the patient's esophagus. A neonate's chest is relatively thin and translucent. Light source 66, if bright enough, can be seen through the neonate's chest, and the caregiver can visually verify the position of tip 12. Light source 66 may be illuminated by a lamp outside proximal portion 14 and an optic fiber running the length of feeding tube 10. It is also contemplated that a fiber optic camera (not shown) could be located at or fiber optically connected to tip 12 and used as a traditional endoscope to aid in positioning feeding tube 10. In some embodiments, the fiber optic device is a permanent part of feeding tube 10, whereas, in alternative embodiments, the fiber optic device is inserted into a feeding lumen 36 prior to placement in the body and removed after feeding tube 10 is properly placed, so that the lumen 36 may be used for feeding.

When feeding tube 10 is inserted, it is important to follow the esophagus and not veer into the lungs. One way to tell which path is being followed is by a temperature measurement with thermistors at tip 12. If different temperatures are measured with inhale and exhale respiration, the tip is in an air passage. If the temperature is constant, the tip is in the esophagus. Monitoring pressure at tip 12 can be used analogously. Pressure can be measured by sealing one of the lumens and adding a pressure port.

Another aid in positioning feeding tube 10 is to include a sensor that measures pH. If tip 12 is properly in the stomach, the measured pH should be acidic. If tip 12 is in the lungs, the measured pH will be neutral. If tip 12 is in the esophagus, the measured pH will be somewhat acidic, depending on reflux, etc.

The esophageal temperature probe and feeding tube described herein and in U.S. Published Patent Application No. 2011/0084881 comprise physiologically acceptable materials that can be sterilized. In particular, all sensing elements, such as electrodes and thermistors, should preferably be soft, flexible, and biocompatible.

According to an aspect of the invention, feeding tube 10 has sensors such as electrodes and thermistors that register parameters such as temperature, pressure, pH, or capacitance. One or more of such parameters can be measured and then analyzed to determine whether feeding occurred. If it is determined that feeding occurred, this determination results in the prevention or suppression of a false alarm.

Figure 3:
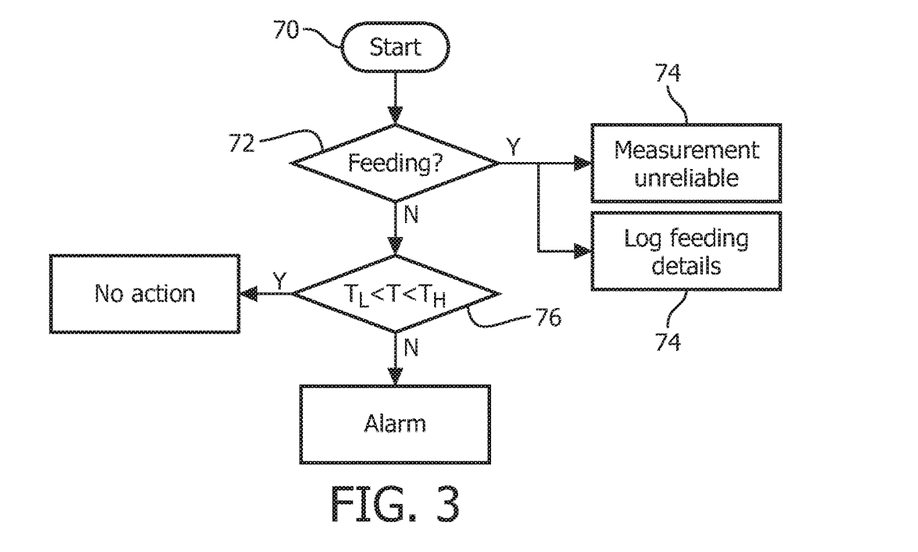
FIG. 3 is a flow chart representing the use of a neonatal temperature probe and feeding tube according to the invention.

FIG. 3 is a flow chart that broadly represents care of a neonatal that incorporates the invention described and claimed herein. The start of the process is the measurement of one or more signals from one or more thermistors or sensors at step 70, leading to analysis in a processor or monitor in step 72. If the processor or monitor determines that there was feeding, the temperature measurement is categorized as "unreliable" as in step 74, whereupon an alarm is suppressed or prevented. In addition, in step 74 the feeding details, such as time, duration, etc., are logged automatically, which is a highly advantageous feature of this invention. If the processor, monitor, or controller determines that feeding did not occur, a temperature signal is sent to step 76, where the system checks to see whether the temperature measured is within pre-set limits ($T_L$=lower temperature limit, $T_H$=upper temperature limit). If the measured temperature is within the pre-set limits, no action is taken. However, if the measured temperature is not within the pre-set limits, an alarm signal is triggered.

As mentioned above, an important aspect of the invention set forth herein is to prevent or suppress false alarms that can result when feeding a neonate. As set forth above, a useful feeding tube comprises thermal sensors or thermistors (such as thermistors 22, 24, 28, 30) placed at different locations along the exterior of feeding tube 10 to measure the (core) temperature of a neonate at those locations. In addition, two pressure ports (sub-diaphragmatic port 32 and supra-diaphragmatic port 34) are included to extract the neonate's respiration effort. In one embodiment a feeding period is detected by utilizing these existing sensing elements. The basic principle is that food, breast milk, or other nutritional liquids or semi-liquids flowing though the feeding tube will create a short pulse in the signal difference between sensors along the feeding tube.

This embodiment will be explained by using thermistors. However, in principle all other sensing elements mentioned above can be used.

Figure 4A:
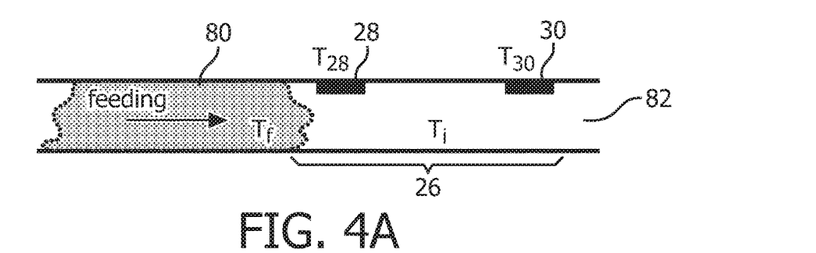
FIG. 4A is a schematic representation of a portion of a cross-sectional view of a feeding tube of FIG. 2.
Figure 4B:
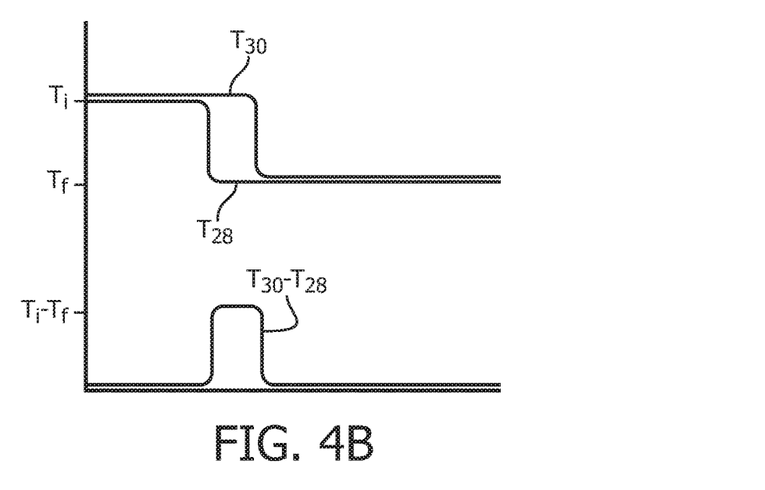
FIG. 4B is a graph that represents temperature measurements and calculations during feeding according an embodiment of the invention.

In the description above, hypopharynx thermistor 28 and oropharynx thermistor 30 are included in nasopharyngeal section 26 to extract respiration flow by measuring the temperature difference between thermistor 28 and thermistors 30. In the schematic of a cross-section of a portion of feeding tube 10 depicted in FIG. 4A, food 80 having a temperature $T_f$ advances distally through a lumen 82 in feeding tube 10. Thermistors 28 and 30 each register a temperature $T_i$ of an empty feeding tube corresponding to a neonate's internal temperature until each thermistor is in turn contacted by food 80 with temperature $T_f$. The temperatures of the respective thermistors 28 and 30 over time and the difference between the temperatures of thermistor 30 and thermistor 28 are set forth in the graph of FIG. 4B. The pulse in the lower portion of FIG. 4B ($T_i$-$T_f$) is a function of the difference between the neonate's internal temperature, the distance from thermistor 28 to thermistor 30, and the velocity of food 80. A processor, monitor, or controller (not shown) will recognize that the pulse represents feeding and will not send an alarm signal or will otherwise prevent or suppress the generation of an alarm.

Figure 5:
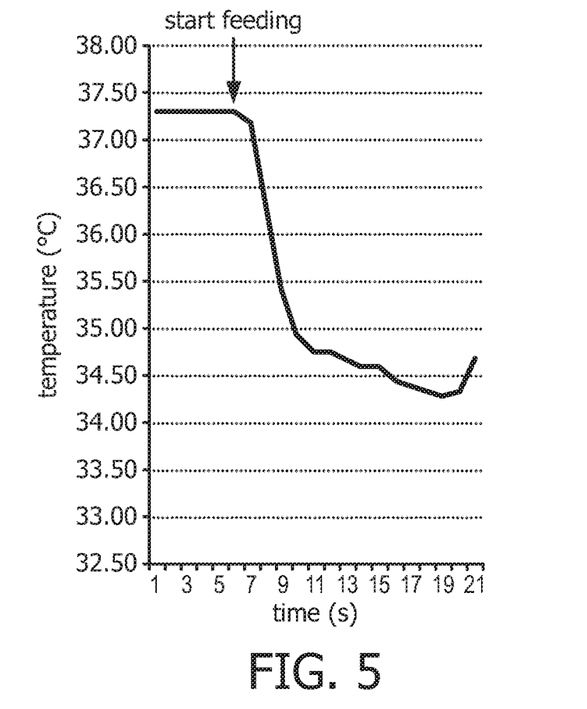
FIG. 5 is a graph that represents temperature versus time during feeding of a neonate.

In another embodiment of the invention, an algorithm is used to recognize feeding with an esophageal feeding tube. Temperature variation in a neonate during feeding as measured by a feeding tube such as described herein, and as set forth in FIG. 5, is totally different from temperature variation in a neonate due to physical or medical problems or issues. After starting the feeding period the temperature drops about 2° C. within 4 seconds (the exact drop mainly depends on the feeding temperature, speed of administration, feeding volume, and the core temperature). This drop is so huge and fast that it cannot be the real core temperature of a neonate. An algorithm in a processor, monitor, or controller (not shown) will evaluate a temperature pattern sensed by, for example, thermistors on a feeding tube 10 and recognize that the pattern represents feeding, not a temperature change of physiological origin. The processor, monitor, or controller will not send an alarm signal or will otherwise prevent or suppress the generation of an alarm. Thus, by means of an algorithm it easily possible to analyze the temperature pattern/course and extract whether or not it was a feeding.

Figure 6A:
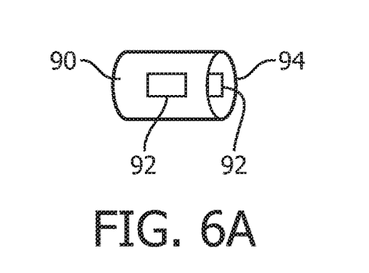
FIGS. 6A and 6B are each a schematic of an oblique view of a section of a cross-sectional view of a feeding tube showing different arrangements of sensors.
Figure 6B:
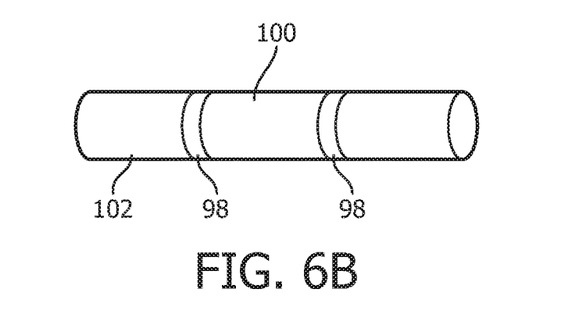

In another embodiment of the invention, impedance measurements can be used to detect feeding. In the section of a feeding tube 90 shown in FIG. 6A, two electrodes 92 are attached to the inner surface 94 of the section. Electrodes 92 are attached by wires (not shown) to a processor, monitor, or controller (not shown), which registers a variation in impedance when food or medicine flows through feeding tube section 90. Similarly, as shown in FIG. 6B, electrodes 98 are positioned on or, preferably, within the outer surface 100 of a section of feeding tube 102. Movement of food or medicine is detected by a galvanic or non-galvanic coupling, that is, capacitance coupling, which causes a variation in impedance that is registered by the processor.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:

1. A method, in a system, of preventing or suppressing a false alarm during administration of food or medicine to a human or animal through a feeding tube having one or more sensors that generate a signal, which method comprises, with a processor, monitor, or controller that generates an alarm:
   analyzing the signals to determine whether food or medicine is being administered; and
   if it is determined that food or medicine is present, preventing or suppressing the alarm;
   wherein the feeding tube includes at least one temperature sensor and temperatures recorded from that temperature sensor are analyzed by an algorithm to determine whether feeding is occurring.

2. A method, in a system of of preventing or suppressing a false alarm during administration of food or medicine to a human or animal through a feeding tube having one or more sensors that generate a signal, which method comprises, with a processor, monitor, or controller that generates an alarm:
   analyzing the signals to determine whether food or medicine is being administered; and
   if it is determined that food or medicine is present, preventing or suppressing the alarm;
   wherein the feeding tube has at least two temperature sensors and there are differences in the temperatures recorded for the different temperature sensors that indicate that food or medicine was administered.

3. The method of claim 1, wherein the analysis by the algorithm includes analyzing rate and extent of any temperature change to determine whether feeding is occurring.

4. The method of claim 1, which comprises an additional step in which details regarding the feeding are recorded.

5. The method of claim 4, wherein time and length of administration are recorded.

6. The method of claim 1, wherein the human is a neonate and the alarm indicates temperature of the neonate is outside of a pre-set range.

7. A system of preventing or suppressing a false alarm during administration of food or medicine to a patient via a feeding tube, the system comprising:
   at least one sensor configured to generate a signal, the at least one sensor being disposed on a portion of the feeding tube; and
   at least one electronic processor programmed to:
      analyze the signal from the at least one sensor to determine whether food or medicine is being administered;
      determine whether a temperature indicated by the signal from the at least one sensor is outside of a pre-set range; and
      generating an alarm if the temperature indicated by the signal from the at least one sensor is outside of the pre-set range except preventing or suppressing the alarm when the analysis of the signal from the at least one sensor determines that food or medicine is being administered.

8. The system of claim 7, wherein the at least one sensor comprises at least two temperature sensors, and the at least one electronic processor is programmed to:
   analyze differences in temperature values measured by the at least two temperature sensors to determine whether food or medicine was administered.

9. The system of claim 7, wherein the at least one sensor comprises a temperature sensor, and the at least one electronic processor is programmed to:

compare a measured temperature value by the temperature sensor to a threshold temperature value to determine whether feeding occurred.

10. The system of claim 9, wherein the at least one electronic processor is programmed to:
analyze a rate and extent of any temperature change with an algorithm to determine whether feeding is occurring.

11. The system of claim 7, wherein the at least one sensor comprises two or more electrodes configured to sense a change in impedance in the associated feeding tube, and the at least one electronic processor is programmed to:
analyze the change in impedance to determine whether food or medicine is being administered.

12. A method, in a system, of preventing or suppressing a false alarm during administration of food or medicine to a human or animal through a feeding tube having one or more sensors that generate a signal, which method comprises, with a processor, monitor, or controller that generates an alarm:
analyzing the signals to determine whether food or medicine is being administered; and
if it is determined that food or medicine is present, preventing or suppressing the alarm;
wherein the sensors include two or more electrodes that sense a change in impedance and the analyzing includes analyzing the change in impedance to determine whether food or medicine is being administered.

* * * * *